United States Patent
Shee et al.

(10) Patent No.: US 10,301,689 B1
(45) Date of Patent: May 28, 2019

(54) METHODS AND COMPOSITIONS FOR DETECTION OF ZIKA VIRAL INFECTIONS

(71) Applicant: Theranos IP Company, LLC, Healdsburg, CA (US)

(72) Inventors: Chandan Shee, Newark, CA (US); Jerzy Majka, Foster City, CA (US); Bernardo Araujo, Mountain View, CA (US); Ushati Das Chakravarty, Mountain View, CA (US); Katrina Sullivan-Bibee, Palo Alto, CA (US); Jerald Sapida, San Leandro, CA (US); Kristine Salazar, Fremont, CA (US)

(73) Assignee: Theranos IP Company, LLC, New York, NY (US)

( * ) Notice: Subject to any disclaimer, the term of this patent is extended or adjusted under 35 U.S.C. 154(b) by 0 days.

(21) Appl. No.: 15/664,807

(22) Filed: Jul. 31, 2017

Related U.S. Application Data

(60) Provisional application No. 62/369,179, filed on Jul. 31, 2016, provisional application No. 62/369,009, filed on Jul. 29, 2016, provisional application No. 62/368,961, filed on Jul. 29, 2016, provisional application No. 62/368,995, filed on Jul. 29, 2016, provisional application No. 62/369,006, filed on Jul. 29, 2016.

(51) Int. Cl.
*A61K 39/12* (2006.01)
*A61K 39/00* (2006.01)
*C12Q 1/70* (2006.01)
*C12N 7/00* (2006.01)
*A61K 39/295* (2006.01)

(52) U.S. Cl.
CPC .................................. *C12Q 1/701* (2013.01)

(58) Field of Classification Search
CPC ...... C12N 7/00; A61K 39/12; A61K 2039/53; C07K 14/005; Y02A 50/394
See application file for complete search history.

(56) References Cited

FOREIGN PATENT DOCUMENTS

CN 105734171 A * 7/2016

* cited by examiner

*Primary Examiner* — Barry A Chestnut

(57) ABSTRACT

Applicant discloses herein kits for identifying the presence of Zika virus in a sample. In embodiments, these kits comprise reagents disclosed herein. Applicant further provides kits for use in detecting ZIKV in a sample, the kits comprising reagents disclosed herein. In embodiments, kits include primers directed to Zika virus (ZIKV) nucleic acid sequences, the primers capable of hybridizing to ZIKV nucleic acids and to copies of ZIKV nucleic acids (including to cDNA copies of ZIKV nucleic acids). Applicant discloses herein reagents for detecting Zika virus (ZIKV) in a sample, the reagents including one or more nucleic acid primers that are capable of hybridizing to a ZIKV nucleic acid (including to cDNA copies of ZIKV nucleic acids).

20 Claims, 2 Drawing Sheets

Specification includes a Sequence Listing.

SEQUENCE LISTING

```
<160> NUMBER OF SEQ ID NOS: 8

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gacatggctt cggacag                                                17

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atattgagtg tctgattgct tg                                          22

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
tgcccaacac aaggtgaagc c                                           21

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aacgagtcat atgaatttag gc                                          22

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 5
gcagcccgat ctattttatt at                                              22

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
agggaacgga gtgtttacag ttcc                                            24

<210> SEQ ID NO 7
<211> LENGTH: 672
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7
```

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Pro Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asn Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

```
Leu Leu Lys Glu Gly Gln Arg Trp Leu Thr Glu Ala Arg Lys Glu Thr
            275                 280                 285

Val Met Gly Gln Pro Thr Pro Lys Thr Pro Arg Gln Leu Arg Glu Phe
        290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Asp Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
            580                 585                 590

His Ile His Gly Glu Ile Tyr Arg Arg Arg Gly Leu Leu Thr Ser Lys
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

<210> SEQ ID NO 8
<211> LENGTH: 867
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 8

Met Gly His His His His His His His His Ser Ser Gly His
1               5                   10                  15

Ile Glu Gly Arg Ala Ser Ser Gly His Glu Asn Leu Tyr Phe Gln
            20                  25                  30

Ser Met Gly Met Arg Gly Met Leu Pro Leu Phe Glu Pro Lys Gly Arg
        35                  40                  45

Val Leu Leu Val Asp Gly His His Leu Ala Tyr Arg Thr Phe His Ala
50                  55                  60

Leu Lys Gly Leu Thr Thr Ser Arg Gly Glu Pro Val Gln Ala Val Tyr
65                  70                  75                  80

Gly Phe Ala Lys Ser Leu Leu Lys Ala Leu Lys Glu Asp Gly Asp Ala
                85                  90                  95

Val Ile Val Val Phe Asp Ala Lys Ala Pro Ser Phe Arg His Glu Ala
                100                 105                 110

Tyr Gly Gly Tyr Lys Ala Gly Arg Ala Pro Thr Pro Glu Asp Phe Pro
                115                 120                 125

Arg Gln Leu Ala Leu Ile Lys Glu Leu Val Asp Leu Leu Gly Leu Ala
130                 135                 140

Arg Leu Glu Val Pro Gly Tyr Glu Ala Asp Asp Val Leu Ala Ser Leu
145                 150                 155                 160

Ala Lys Lys Ala Glu Lys Glu Gly Tyr Glu Val Arg Ile Leu Thr Ala
                165                 170                 175

Asp Lys Asp Leu Tyr Gln Leu Leu Ser Asp Arg Ile His Val Leu His
                180                 185                 190

Pro Glu Gly Tyr Leu Ile Thr Pro Ala Trp Leu Trp Glu Lys Tyr Gly
                195                 200                 205

Leu Arg Pro Asp Gln Trp Ala Asp Tyr Arg Ala Leu Thr Gly Asp Glu
210                 215                 220

Ser Asp Asn Leu Pro Gly Val Lys Gly Ile Gly Glu Lys Thr Ala Arg
225                 230                 235                 240

Lys Leu Leu Glu Glu Trp Gly Ser Leu Glu Ala Leu Leu Lys Asn Leu
                245                 250                 255

Asp Arg Leu Lys Pro Ala Ile Arg Glu Lys Ile Leu Ala His Met Asp
                260                 265                 270

Asp Leu Lys Leu Ser Trp Asp Leu Ala Lys Val Arg Thr Asp Leu Pro
                275                 280                 285

Leu Glu Val Asp Phe Ala Lys Arg Arg Glu Pro Asp Arg Glu Arg Leu
290                 295                 300

Arg Ala Phe Leu Glu Arg Leu Glu Phe Gly Ser Leu Leu His Glu Phe
305                 310                 315                 320

Gly Leu Leu Glu Ser Pro Lys Ala Leu Glu Glu Ala Pro Trp Pro Pro
                325                 330                 335

Pro Glu Gly Ala Phe Val Gly Phe Val Leu Ser Arg Lys Glu Pro Met
                340                 345                 350

Trp Ala Asp Leu Leu Ala Leu Ala Ala Ala Arg Gly Gly Arg Val His
                355                 360                 365

Arg Ala Pro Glu Pro Tyr Lys Ala Leu Arg Asp Leu Lys Glu Ala Arg
370                 375                 380

```
Gly Leu Leu Ala Lys Asp Leu Ser Val Leu Ala Arg Glu Gly Leu
385                 390                 395                 400

Gly Leu Pro Pro Gly Asp Asp Pro Met Leu Leu Ala Tyr Leu Leu Asp
            405                 410                 415

Pro Ser Asn Thr Thr Pro Glu Gly Val Ala Arg Arg Tyr Gly Gly Glu
            420                 425                 430

Trp Thr Glu Glu Ala Gly Glu Arg Ala Ala Leu Ser Glu Arg Leu Phe
        435                 440                 445

Ala Asn Leu Trp Gly Arg Leu Glu Gly Glu Glu Arg Leu Leu Trp Leu
        450                 455                 460

Tyr Arg Glu Val Glu Arg Pro Leu Ser Ala Val Leu Ala His Met Glu
465                 470                 475                 480

Ala Thr Gly Val Arg Leu Asp Val Ala Tyr Leu Arg Ala Leu Ser Leu
            485                 490                 495

Glu Val Ala Glu Glu Ile Ala Arg Leu Glu Ala Glu Val Phe Arg Leu
            500                 505                 510

Ala Gly His Pro Phe Asn Leu Asn Ser Arg Asp Gln Leu Glu Arg Val
        515                 520                 525

Leu Phe Asp Glu Leu Gly Leu Pro Ala Ile Gly Lys Thr Glu Lys Thr
530                 535                 540

Gly Lys Arg Ser Thr Ser Ala Ala Val Leu Glu Ala Leu Arg Glu Ala
545                 550                 555                 560

His Pro Ile Val Glu Lys Ile Leu Gln Tyr Arg Glu Leu Thr Lys Leu
            565                 570                 575

Lys Ser Thr Tyr Ile Asp Pro Leu Pro Asp Leu Ile His Pro Arg Thr
            580                 585                 590

Gly Arg Leu His Thr Arg Phe Asn Gln Thr Ala Thr Ala Thr Gly Arg
        595                 600                 605

Leu Ser Ser Ser Asp Pro Asn Leu Gln Asn Ile Pro Val Arg Thr Pro
        610                 615                 620

Leu Gly Gln Arg Ile Arg Arg Ala Phe Ile Ala Glu Glu Gly Trp Leu
625                 630                 635                 640

Leu Val Ala Leu Asp Tyr Ser Gln Ile Glu Leu Arg Val Leu Ala His
            645                 650                 655

Leu Ser Gly Asp Glu Asn Leu Ile Arg Val Phe Gln Glu Gly Arg Asp
            660                 665                 670

Ile His Thr Glu Thr Ala Ser Trp Met Phe Gly Val Pro Arg Glu Ala
        675                 680                 685

Val Asp Pro Leu Met Arg Arg Ala Ala Lys Thr Ile Asn Phe Gly Val
        690                 695                 700

Leu Tyr Gly Met Ser Ala His Arg Leu Ser Gln Glu Leu Ala Ile Pro
705                 710                 715                 720

Tyr Glu Glu Ala Gln Ala Phe Ile Glu Arg Tyr Phe Gln Ser Phe Pro
            725                 730                 735

Lys Val Arg Ala Trp Ile Glu Lys Thr Leu Glu Glu Gly Arg Arg Arg
            740                 745                 750

Gly Tyr Val Glu Thr Leu Phe Gly Arg Arg Arg Tyr Val Pro Asp Leu
        755                 760                 765

Glu Ala Arg Val Lys Ser Val Arg Glu Ala Ala Glu Arg Met Ala Phe
        770                 775                 780

Asn Met Pro Val Gln Gly Thr Ala Ala Asp Leu Met Lys Leu Ala Met
785                 790                 795                 800

Val Lys Leu Phe Pro Arg Leu Glu Glu Met Gly Ala Arg Met Leu Leu
```

-continued

```
            805                 810                 815
Gln Val His Asp Glu Leu Val Leu Glu Ala Pro Lys Glu Arg Ala Glu
            820                 825                 830

Ala Val Ala Arg Leu Ala Lys Glu Val Met Glu Gly Val Tyr Pro Leu
            835                 840                 845

Ala Val Pro Leu Glu Val Glu Val Gly Ile Gly Glu Asp Trp Leu Ser
    850                 855                 860

Ala Lys Glu
865
```

METHODS AND COMPOSITIONS FOR DETECTION OF ZIKA VIRAL INFECTIONS

CROSS-REFERENCE

This application claims priority to U.S. Application Nos. 62/368,961 filed Jul. 29, 2016, 62/368,995 filed Jul. 29, 2016, 62/369,006 filed Jul. 29, 2016, 62/369,179 filed Jul. 31, 2016, and 62/369,009 filed Jul. 29, 2016. All of the foregoing applications and patents are incorporated herein by reference in their entirety for all purposes.

SEQUENCE LISTING

The instant application contains a Sequence Listing which has been submitted electronically in ASCII format and is hereby incorporated by reference in its entirety. Said ASCII copy, created on Nov. 17, 2017, is named 3055_201_SL.txt and is 15,171 bytes in size.

BACKGROUND

A variety of methods for the amplification of nucleic acids are known. For example, polymerase chain reaction ("PCR") (see, e.g. U.S. Pat. No. 4,683,202) is a popular method for the amplification of nucleic acids. PCR methods are in vitro methods able to amplify a specific polynucleotide sequence. PCR can be used to amplify specific polynucleotide sequences, including genomic DNA, single-stranded cDNA, and mRNA among others. As described in U.S. Pat. No. 4,683,202, U.S. Pat. No. 4,683,195, and U.S. Pat. No. 4,800,159 (hereby incorporated herein by reference), PCR typically comprises treating separate complementary strands of a target nucleic acid with two polynucleotide primers to form complementary primer extension products on both strands that act as templates for synthesizing copies of the desired nucleic acid sequences. By repeating the separation and synthesis steps in an automated system, essentially exponential duplication of the target sequences can be achieved.

To successfully perform a PCR reaction, the reaction must be performed at multiple different temperatures. This requires hardware or other mechanisms for repeatedly changing the temperature of the PCR reaction. In embodiments where the target nucleic acid is RNA, reverse transcription PCR (rtPCR) may be used.

Zika virus (ZIKV) is a member of the Flavivirus genus of viruses (family Flaviviridae). Other members of the genus include dengue virus (DENV), West Nile Virus (WNV), Japanese encephalitis virus (JEV), yellow fever virus (YFV), and tick-borne encephalitic virus (TBEV). Flaviviruses have a single-strand, positive-sense RNA genome that serves both as a genome and messenger RNA. The RNA genome is translated into a single polyprotein that is proteolytically cleaved into three structural proteins (capsid, prM, and envelope) and non-structural proteins NS1 to NS5. The virion contains a nucleocapsid composed of the capsid protein (C) and the RNA genome, surrounded by an icosahedral shell comprising both the envelope (E) glycoprotein and membrane (M) protein or the precursor membrane (prM) protein anchored in a lipid membrane.

Flaviviruses may be transmitted by the bite from an infected arthropod (e.g., mosquito or tick) and may cause widespread morbidity and mortality throughout the world. Most recently, the Zika virus has spread rapidly across the Americas following its introduction into Brazil in 2015. While Zika virus disease is usually mild with non-specific symptoms, such as fever, rash, conjunctivitis, and muscle and joint pain, there have been more severe conditions linked to the Zika virus, such as congenital microcephaly in newborns and Guillain-Barré syndrome (GBS) in adults. Thus, it has become increasingly important to be able to detect Zika virus infection in an individual.

Currently, Zika virus infection is diagnosed through detection of the viral RNA and virus isolation from blood samples, which can be time consuming. Diagnosis by serology can be difficult as the Zika virus can cross-react with other flaviviruses, such as DENV, WNV, and YFV. Thus, there is a need for better assays that are capable of specifically detecting the Zika virus. Moreover, there is a need for a rapid and simple test for detecting Zika virus infection at or near the point of service.

SUMMARY

In one embodiment, Applicant discloses herein reagents, methods, and kits for detecting Zika virus (ZIKV) in samples of bodily fluid.

Applicant discloses herein reagents for use in PCR methods for detecting Zika virus (ZIKV) in samples of bodily fluid. In embodiments, provided herein is a method for detecting ZIKV in a sample of bodily fluid, the method comprising: A) generating multiple complementary DNA (cDNA) copies of at least portions of ZIKV RNA, B) generating multiple copies of said cDNA copies of ZIKV RNA by polymerase chain reaction (PCR) amplification. In embodiments of the methods disclosed herein, generating multiple complementary DNA (cDNA) copies of at least portions of ZIKV RNA comprises using a reverse transcriptase to effect reverse transcription of said at least portions of ZIKV RNA to provide said cDNA copies of at least portions of ZIKV RNA. In embodiments of the methods for detecting Zika virus (ZIKV) in samples of bodily fluid disclosed herein, the PCR methods comprise reverse transcription PCR (RT-PCR) methods. In embodiments, said cDNA copies comprise a polynucleotide template for PCR amplification. In embodiments of the methods disclosed herein, generating multiple complementary DNA (cDNA) copies of at least portions of ZIKV RNA comprises PCR amplification using a PCR reaction mixture that comprises a PCR amplification reaction first primer and a PCR amplification reaction second primer, wherein in the PCR amplification reaction mixture, the PCR amplification reaction first primer anneals to the polynucleotide template and the PCR second primer anneals to a polynucleotide which is complementary to the polynucleotide template, and wherein in the PCR amplification reaction mixture, multiple copies of a PCR amplification reaction product are formed, wherein the PCR amplification reaction product is a double-stranded nucleic acid molecule comprising a first strand and a second strand, and wherein a first strand of the PCR amplification reaction product is a copy of the polynucleotide template. In embodiments of the methods for detecting Zika virus (ZIKV) in samples of bodily fluid disclosed herein, the PCR methods comprise real-time PCR methods. In embodiments of the methods for detecting Zika virus (ZIKV) in samples of bodily fluid disclosed herein, the PCR methods comprise reverse transcription real-time PCR methods.

In embodiments, a reagent for identifying the presence of ZIKV in a sample comprises a nucleic acid that can serve as a positive control for PCR nucleic amplification assays for identifying the presence of ZIKV in a sample, and for detecting ZIKV in a sample. In embodiments, a reagent for identifying the presence of ZIKV in a sample comprises a nucleic acid that can serve as a positive control for PCR nucleic amplification assays for identifying the presence of ZIKV in a sample, and for detecting ZIKV in a sample, and a buffer.

In embodiments, a reagent for identifying the presence of ZIKV in a sample comprises a buffer and a variant of a nucleic acid sequence that comprises a nucleic acid sequence found in, or is complementary to a nucleic acid sequence found in, or is homologous to a nucleic acid sequence found in, or complementary to a homologous nucleic acid sequence found in, ZIKV. In embodiments, such a nucleic acid sequence variant has at least about 95% sequence identity to the nucleic acid sequence.

In embodiments, a reagent for identifying the presence of ZIKV comprises a buffer selected from phosphate and tris(hydroxymethyl)aminomethane (TRIS). In embodiments, a reagent for identifying the presence of ZIKV comprises a TRIS buffer.

In embodiments, Applicant provides herein reagents for identifying the presence of ZIKV in a sample. In embodiments, a reagent for identifying the presence of ZIKV in a sample comprises a nucleic acid sequence selected from the group SEQ ID NO: 1, SEQ ID NO: 2, SEQ ID NO: 3, SEQ ID NO: 4, SEQ ID NO: 5, and SEQ ID NO: 6, and a buffer. In embodiments, the nucleic acid primer of a reagent as disclosed herein comprises a nucleic acid sequence selected from the group SEQ ID NO: 1, SEQ ID NO: 2, and SEQ ID NO: 3.

In embodiments, a reagent for identifying the presence of ZIKV in a sample comprises a buffer and a variant of a nucleic acid sequence selected from the group SEQ ID NO: 1, SEQ ID NO: 2, SEQ ID NO: 3, SEQ ID NO: 4, SEQ ID NO: 5, and SEQ ID NO: 6, wherein the variant has at least about 95% sequence identity to the nucleic acid sequence. In embodiments, the nucleic acid primer of a reagent as disclosed herein comprises a variant of a nucleic acid sequence selected from the group SEQ ID NO: 1, SEQ ID NO: 2, and SEQ ID NO: 3, wherein the variant has at least about 95% sequence identity to the nucleic acid sequence.

In embodiments, a reagent for identifying the presence of ZIKV comprises a buffer selected from phosphate and tris(hydroxymethyl)aminomethane (TRIS). In embodiments, a reagent for identifying the presence of ZIKV comprises a TRIS buffer.

In embodiments of reagents for identifying the presence of ZIKV as disclosed herein, the primer comprises a reporter molecule. In embodiments wherein the primer comprises a reporter molecule, the reporter molecule may comprise a fluorescent moiety. In embodiments wherein the primer comprises a fluorescent moiety, the nucleic acid primer may further comprise a quenching moiety effective to quench fluorescence from the fluorescent moiety when the primer is not hybridized to a target nucleic acid sequence.

Applicant discloses herein kits for detecting Zika virus (ZIKV) in samples of bodily fluid. Kits for detecting Zika virus (ZIKV) in samples include reagents as disclosed herein. Kits for detecting Zika virus (ZIKV) in samples include nucleic acids as disclosed herein. Kits for detecting Zika virus (ZIKV) in samples include nucleic acid primers as disclosed herein. Kits for detecting Zika virus (ZIKV) in samples include nucleic acids comprising reporter molecules as disclosed herein. Kits for detecting Zika virus (ZIKV) in samples include nucleic acid primers comprising reporter molecules as disclosed herein.

The assays and methods disclosed herein may be performed on a device, or on a system, for processing a sample. The assays and methods disclosed herein can be readily incorporated into and used in an automated assay device, and in an automated assay system. The assays and methods disclosed herein can be readily incorporated into and used in an automated sample analysis device. For example, devices and systems as disclosed herein may include a communication assembly for transmitting or receiving a protocol based on the analyte to be detected (e.g., ZIKV) or based on other analytes to be detected by the device or system.

Methods and compositions disclosed herein provide rapid assays which require only small amounts of sample, such as only small amounts of blood. Device and systems disclosed herein are configured to perform such rapid assays which require only small amounts of sample, such as only small amounts of blood. Accordingly, the methods, compositions, devices, and systems provide rapid tests, which require only small biological samples, and thus provide advantages over other methods, reagents, kits, assays, devices, and systems.

DETAILED DESCRIPTION

Figure 1:
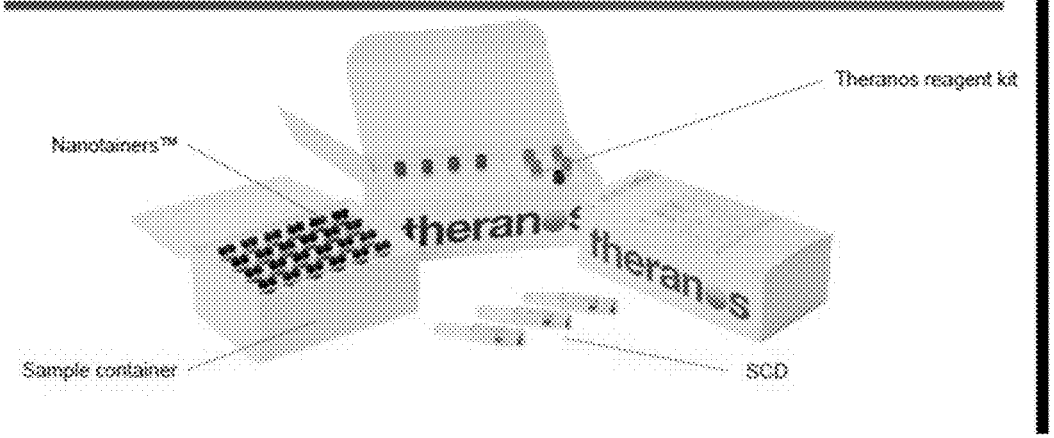
FIG. 1 shows a perspective image of a rRT-PCR Reagent kit and related articles, as disclosed herein.

It is to be understood that both the foregoing general description and the following detailed description are exemplary and explanatory only and are not restrictive of the invention, as claimed. It may be noted that, as used in the specification and the appended claims, the singular forms "a", "an" and "the" include plural referents unless the context clearly dictates otherwise. Thus, for example, reference to "a material" may include mixtures of materials, reference to "a compound" may include multiple compounds, and the like. References cited herein are hereby incorporated by reference in their entirety, except to the extent that they conflict with teachings explicitly set forth in this specification.

In this specification and in the claims which follow, reference will be made to a number of terms which shall be defined to have the following meanings:

As used herein, a "sample" may be, but is not limited to, blood, cerebrospinal fluid, bile, plasma, serum, saliva, sputum, mucus, and urine, or any portion thereof. The sample may be of any suitable size or volume. In some embodiments of the assays and methods disclosed herein, measurements may be made using a small volume of the sample, or no more than a small volume portion of the sample, where a small volume comprises no more than about 5 mL; or comprises no more than about 3 mL; or comprises no more than about 2 mL; or comprises no more than about 1 mL; or comprises no more than about 500 µL; or comprises no more than about 250 µL; or comprises no more than about 100 µL; or comprises no more than about 75 µL; or comprises no more than about 50 µL; or comprises no more than about 35 µL; or comprises no more than about 25 µL; or comprises no more than about 20 µL; or comprises no more than about 15 µL; or comprises no more than about 10 µL; or comprises no more than about 8 µL; or comprises no more than about 6 µL; or comprises no more than about 5 µL; or comprises no more than about 4 µL; or comprises no more than about 3

µL; or comprises no more than about 2 µL; or comprises no more than about 1 µL; or comprises no more than about 0.8 µL; or comprises no more than about 0.5 µL; or comprises no more than about 0.3 µL; or comprises no more than about 0.2 µL; or comprises no more than about 0.1 µL; or comprises no more than about 0.05 µL; or comprises no more than about 0.01 µL.

As used herein, the term "analyte" refers to a molecule of interest that is detected or to be detected in an analytical procedure.

As used in the description herein and throughout the claims that follow, the meaning of "or" includes both the conjunctive and disjunctive unless the context expressly dictates otherwise. Thus, the term "or" includes "and/or" unless the context expressly dictates otherwise.

The term "moiety" as used herein refers to any particular composition of matter, e.g., a molecular fragment, an intact molecule, or a mixture of materials.

As used herein, "nucleic acid" includes both DNA and RNA, including DNA and RNA containing non-standard nucleotides. A "nucleic acid" contains at least one polynucleotide (a "nucleic acid strand"). A "nucleic acid" may be single-stranded or double-stranded. This, the term "nucleic acid" refers to nucleotides and nucleosides which make up, for example, deoxyribonucleic acid (DNA) macromolecules and ribonucleic acid (RNA) macromolecules. Nucleic acids may be identified by the base attached to the sugar (e.g., deoxyribose or ribose); as used herein, the abbreviations for these bases (shown in Table 1) are used to represent nucleic acids in sequence listings identifying and describing their structures (either upper-case or lower-case may be used).

TABLE 1

| Base (in Nucleic Acid) | Letter Code |
|---|---|
| Adenine | A |
| Thymine | T |
| Guanine | G |
| Cytosine | C |
| Uracil | U |

RNA molecules found in nature consist of sequences of A, G, C, and U, while DNA molecules found in nature consist of A, G, C, and T; that is, where a RNA sequence that is complementary to a nucleic acid target sequence includes U, a DNA sequence that is complementary to that nucleic acid target sequence includes T in place of U.

As used herein, the term "polynucleotide" is used to refer to a polymeric chain containing two or more nucleotides. "Polynucleotides" include primers, oligonucleotides, nucleic acid strands, etc. A polynucleotide may contain standard or non-standard nucleotides. Typically, a polynucleotide contains a 5' phosphate at one terminus ("5' terminus") and a 3' hydroxyl group at the other terminus ("3' terminus) of the chain. The most 5' nucleotide of a polynucleotide may be referred to herein as the "5' terminal nucleotide" of the polynucleotide. The most 3' nucleotide of a polynucleotide may be referred to herein as the "3' terminal nucleotide" of the polynucleotide.

The term "downstream" as used herein in the context of a polynucleotide containing a 5' terminal nucleotide and a 3' terminal nucleotide refers to a position in the polynucleotide which is closer to the 3' terminal nucleotide than a reference position in the polynucleotide. For example, in a primer having the sequence: 5' ATAAGC 3', the "G" is downstream from the "T" and all of the "A"s.

The term "upstream" as used herein in the context of a polynucleotide containing a 5' terminal nucleotide and a 3' terminal nucleotide, refers to a position in the polynucleotide which is closer to the 5' terminal nucleotide than a reference position in the polynucleotide. For example, in a primer having the sequence: 5' TAGC 3', the "T" is upstream from the "G", the "C", and the "A".

As used herein, a nucleic acid molecule which is described as containing the "sequence" of a template or other nucleic acid may also be considered to contain the template or other nucleic acid itself (e.g. a molecule which is described as containing the sequence of a template may also be described as containing the template), unless the context clearly dictates otherwise.

As used herein "cDNA" refers to DNA molecules ("complementary DNA") produced by reverse transcription of an RNA molecule. Such reverse transcription produces a DNA molecule having a nucleotide sequence that is the same as the nucleotide sequence of that RNA molecule, with the exception that where the RNA molecule has a uracil moiety (U) the DNA molecule has instead a thymine (T). A cDNA produced by reverse transcription of an RNA molecule is complementary to the complement of that RNA molecule.

As used herein, a "target" nucleic acid or molecule refers to a nucleic acid of interest. A target nucleic acid/molecule may be of any type, including single-stranded or double stranded DNA or RNA (e.g. mRNA). In some instances, a target nucleic acid may be a nucleic acid which may directly function as a double-stranded nucleic acid template in a method provided herein (e.g. a double-stranded DNA molecule), or it may be a nucleic acid which requires further processing or conversion to function as a double-stranded nucleic acid template in a method provided herein (e.g. mRNA).

As used herein, "complementary" sequences refer to two nucleotide sequences which, when aligned anti-parallel to each other, contain multiple individual nucleotide bases which pair with each other. It is not necessary for every nucleotide base in two sequences to pair with each other for sequences to be considered "complementary". Sequences may be considered complementary, for example, if at least 30%, 40%, 50%, 55%, 60%, 65%, 70%, 75%, 80%, 85%, 90%, 95%, 98%, 99%, or 100% of the nucleotide bases in two sequences pair with each other. In addition, sequences may still be considered "complementary" when the total lengths of the two sequences are significantly different from each other. For example, a primer of 15 nucleotides may be considered "complementary" to a longer polynucleotide containing hundreds of nucleotides if multiple individual nucleotide bases of the primer pair with nucleotide bases in the longer polynucleotide when the primer is aligned anti-parallel to a particular region of the longer polynucleotide.

"Identical" or "identity," as used herein in the context of two or more polypeptide or polynucleotide sequences, can mean that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation.

"Homology" or "homologous" as used herein in the context of two or more polypeptide or polynucleotide sequences, can mean that the sequences have a specified percentage of residues that are either i) the same, or ii) conservative substitutions of the same residue, over a specified region. Conservative substitutions include substitutions of one amino acid by an amino acid of the same group, and include substitutions of one amino acid by an amino acid as an exemplary or as a preferred substitution as known in the art. In determining homology of two sequences, identical residues and homologous residues are given equal weight. The percentage can be calculated by optimally aligning the two sequences, comparing the two sequences over the specified region, determining the number of positions at which either identical or homologous residues occur in both sequences to yield the number of matched positions, dividing the number of matched positions by the total number of positions in the specified region, and multiplying the result by 100 to yield the percentage of sequence homology. In cases where the two sequences are of different lengths or the alignment produces one or more staggered ends and the specified region of comparison includes only a single sequence, the residues of the single sequence are included in the denominator but not the numerator of the calculation.

As used herein, in the context of two or more polymeric molecules (e.g. nucleic acids, proteins), "corresponds to", "corresponding to", and the like refers to polymeric molecules or portions thereof which have the same or similar sequence of component elements (e.g. nucleotides, amino acids). For example, if a first nucleic acid is described as containing a region which "corresponds to" the sequence of a second nucleic acid, the relevant region of the first nucleic acid has a nucleotide sequence which is the same or similar to the sequence of the second nucleic acid.

The term "primer" as used herein refers to a polynucleotide, whether occurring naturally as in a purified restriction digest or produced synthetically, which is capable of acting as a point of initiation of synthesis when placed under conditions in which synthesis of a primer extension product which is complementary to a nucleic acid strand is induced, i.e., in the presence of nucleotides and an inducing agent such as DNA polymerase and at a suitable temperature and pH. The primer is preferably single stranded for maximum efficiency in amplification, but may alternatively be double stranded. If double stranded, the primer is first treated to separate its strands before being used to prepare extension products. Preferably, the primer is a poly-deoxyribonucleotide. The primer must be sufficiently long to prime the synthesis of extension products in the presence of the inducing agent. The exact lengths of the primers will depend on many factors, including temperature, source of primer and use of the method. For example, for diagnostics applications, depending on the complexity of the target sequence, the polynucleotide primer typically contains about 10-30 or more nucleotides, or about 15-25 or more nucleotides, although it may contain fewer nucleotides. For other applications, the polynucleotide primer is typically shorter, e.g., 7-15 nucleotides. Such short primer molecules generally require cooler temperatures to form sufficiently stable hybrid complexes with template.

A primer may include a marker moiety, such as a fluorescent moiety, or a quencher moiety (e.g., for quenching fluorescence by fluorescence (or Forster) resonance energy transfer FRET)), or combinations thereof. Fluorescein dyes (e.g., FAM™) are suitable fluorescent moieties ("dye"). Other suitable dyes include VIC®, ROX™, SYBR® Green, JOE, TAMRA™, and NED™ dyes, all of which are commercially available and may be linked to nucleic acid molecules. Dabcyl (4-((4-(dimethylamino)phenyl)azo)benzoic Acid) is an example of a suitable quencher which is commercially available and may be linked to nucleic acid molecules.

As used herein, when a first polynucleotide is described as "annealed", "annealing" or the like to a second polynucleotide, the entirety of the first polynucleotide or any portion thereof may anneal to the second polynucleotide, and vice versa.

The "Tm" indicates the annealing temperature for a particular primer set; a primer set may have a different Tm than other primer sets, or may have the same Tm as another primer set. In many cases, Tm is typically between about 45° C. to about 80° C., or between about 50° C. to about 75° C.

As used herein, "reverse transcriptase" (RT) refers to an enzyme which can be used to produce a DNA molecule that is complementary to a RNA molecule. The act of producing such a DNA molecule from an RNA template is termed "reverse transcription".

As used herein, polymerase chain reaction, abbreviated by the acronym "PCR", refers to any of the nucleic acid amplification methods in which a target nucleic acid (typically a double-stranded deoxyribonucleic acid) is exposed to a thermostable DNA polymerase during multiple thermal cycles, and in which multiple copies of the target nucleic acid (typically including copies of nucleic acid sequences disposed between a first target region on one strand of a double-stranded target nucleic acid and a second target region on the complementary strand of a double-stranded target nucleic acid) are produced, amplifying the target nucleic acid. Thermal cycles typically include low temperature portions (typically at temperatures between about 40° C. and about 59° C., or between about 45° C. and about 55° C.), intermediate temperature portions (typically at temperatures between about 60° C. and about 74° C.), and higher temperature portions (typically at temperatures between about 75° C. and about 99° C., or between about 80° C. and about 95° C.). For example, some PCR reactions include a) incubation of a mixture including target molecules and primers at high temperature (e.g., about 90° C. to about 95° C.) to denature the target DNA; b) cooling the mixture to an intermediate temperature (e.g., about 50° C. to about 60° C.) to allow annealing between the primers and target DNA; and c) in the presence of DNA polymerase, generating extensions of the primers (e.g., by action of the polymerase at, e.g. temperatures of about 65° C. to about 75° C.); and repeating this cycle of steps a), b), and c). Steps a), b), and c) together may be termed a "thermal cycle".

Amplification occurs with each thermal cycle, and, following multiple cycles, significant amplification of the target nucleic acid molecule produces large numbers of DNA copies of the target sequence. PCR requirements include a DNA polymerase (e.g., a thermostable DNA polymerase), deoxynucleotides, and appropriate buffer solutions. Where a target nucleic acid is an RNA target, reverse transcriptase (RT) may be used to produce a DNA copy of the RNA, and PCR applied to the DNA copies.

As used herein, reverse transcription PCR (RT-PCR) refers to methods for amplifying RNA targets, in which copy DNA molecules (cDNAs) are produced from RNA target polynucleotides by application of reverse transcriptase, and PCR is applied to the cDNA copies to amplify the cDNA copies for detection and/or amplification of the target polynucleotide. RT-PCR requirements include a reverse transcriptase, a DNA polymerase (e.g., a thermostable DNA polymerase), deoxynucleotides (typically as deoxynucleotide tri-phosphates ("dNTPs") such as dATP, dTTP, dGTP, and dCTP), and appropriate buffer solutions.

As used herein, "real-time PCR" refers to PCR amplification methods in which the progress, or extent, of target amplification is monitored during the course of the assay (e.g., at each thermal cycle). Progress of the amplification reactions may be monitored, for example, detecting the amount of fluorescence or absorbance of reporter molecules. Suitable reporter molecules include intercalating dyes (which are detectable when bound to double-stranded DNA, or to the minor groove of DNA, such as ethidium bromide and SYBR Green dye); fluorogenic probes, such as self-quenching dyes, or dye pairs (the pairs including a dye and a quencher) attached to primers (which fluoresce when the primer is bound to target, but do not produce significant fluorescence when not hybridized to target nucleic acid molecules); and other reporter molecules.

As used herein, "rRT-PCR" refers to reverse-transcription real-time PCR. rRT-PCR is real-time PCR applied to RNA targets, using reverse-transcription PCR to amplify nucleic acids based on RNA target molecules, and monitoring the amplification using real-time PCR methods. As used herein, "rRT-PCR" refers to reverse-transcription real-time PCR. rRT-PCR is real-time PCR applied to RNA targets, using reverse-transcription PCR to amplify nucleic acids based on RNA target molecules, and monitoring the amplification using real-time PCR methods. Reverse-transcription PCR methods provide the DNA substrate required for PCR by contacting a sample, under the appropriate conditions, with a reverse transcriptase and producing cDNA copies of RNA molecules in the sample.

The terms "polypeptide" and "protein" may be used interchangeably to refer to molecules comprised of amino acids linked by peptide bonds. Individual amino acids may be termed "residues" of a polypeptide or protein. The amino acid sequences of polypeptides disclosed herein may be identified by SEQ ID NO: presented as a string of letters, where the letters have the following meanings:

TABLE 1B

| AminoAcid | 3-Letter Code | 1-Letter Code |
| --- | --- | --- |
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Amino acid sequence of polypeptides, including enzymes, may include variants of a parent sequence with substitutions, insertions and deletions as compared to the sequence of the parent polypeptide. Amino acid variants of parent polypeptides may be suitable for the same or similar use as the parent polypeptide. For example, amino acid variants of parent polypeptides having amino acid sequences that are 95% or greater identical or similar to the amino acid sequence of the parent polypeptide may be suitable for the same or similar use as the parent polypeptide.

A composition may include a buffer. Buffers include, without limitation, phosphate, citrate, ammonium, acetate, carbonate, tris(hydroxymethyl)aminomethane (TRIS), (N-morpholino) propanesulfonic acid (MOPS), 3-morpholino-2-hydroxypropanesulfonic acid (MOPSO), 2-(N-morpholino)ethanesulfonic acid (MES), N-(2-Acetamido)-iminodiacetic acid (ADA), piperazine-N,N'-bis(2-ethanesulfonic acid) (PIPES), N-(2-Acetamido)-2-aminoethanesulfonic acid (ACES), cholamine chloride, N,N-Bis(2-hydroxyethyl)-2-aminoethanesulfonic acid (BES), 2-[[1,3-dihydroxy-2-(hydroxymethyl)propan-2-yl]amino]ethanesulfonic acid (TES), 4-(2-hydroxyethyl)-1-piperazine ethanesulfonic acid (HEPES), acetamidoglycine, tricine (N-(2-Hydroxy-1,1-bis(hydroxymethyl)ethyl)glycine), glycinamide, and bicine (2-(Bis(2-hydroxyethyl)amino)acetic acid) buffers. Buffers include other organic acid buffers in addition to the phosphate, citrate, ammonium, acetate, and carbonate buffers explicitly mentioned herein.

In embodiments of the compositions disclosed herein, including embodiments of the aqueous compositions and embodiments of the buffered aqueous compositions, the composition may comprise albumin, gelatin, cytochrome C, an immunoglobulin, an amino acid, agar, glycerol, ethylene glycol, a protease inhibitor, an antimicrobial agent, a metal chelating agent, a monosaccharide, a disaccharide, a polysaccharide, a reducing agent, a chelating agent, or combinations thereof.

An article of manufacture may comprise a container; and a composition contained within the container, wherein the composition comprises a nucleic acid molecule (such as, e.g., a primer directed to a target related to ZIKA). An article of manufacture may comprise a container; and a composition contained within the container, wherein the composition comprises a nucleic acid molecule (such as, e.g., a primer directed to a target related to ZIKA). An article of manufacture may comprise a container; and a composition contained within the container, wherein the composition comprises a nucleic acid molecule (such as, e.g., a primer directed to a target related to ZIKA). The containers may be formed from a variety of materials such as glass or plastic, and may have a sterile access port (for example the container may be an intravenous solution bag or a vial having a stopper pierceable by a hypodermic injection needle). The article of manufacture may further comprise a label or package insert on or associated with the container indicating that the composition may be used to detect the presence of a nucleic acid molecule (such as, e.g., a primer directed to a target related to ZIKA) in a sample.

Description and disclosure of examples of reagents, kits, assays, methods, kits, devices, and systems which may use, or be used with, the reagents, kits, methods, devices, and systems disclosed herein may be found, for example, in U.S. Pat. No. 8,088,593; U.S. Pat. No. 8,380,541; U.S. Pat. No. 8,435,738; U.S. Pat. No. 8,475,739; U.S. Pat. No. 8,840,838; U.S. Pat. No. 9,250,229; U.S. Pub. No. 2014/0057255; U.S. Pub. No. 2013/0078624; WO 2013/052318; WO 2014/015199; U.S. patent application Ser. No. 14/183,503, filed Feb. 18, 2014; U.S. patent application Ser. No. 13/933,035, filed Jul. 1, 2013; U.S. patent application Ser. No. 13/769,820, filed Feb. 18, 2013; U.S. patent application Ser. No. 14/183,503, filed Feb. 18, 2014; patent application Ser. No.

14/214,850, filed Mar. 15, 2014; International Patent Application PCT/US2014/030034, filed Mar. 15, 2014; International Patent Application PCT/US2014/056151, filed Sep. 17, 2014; U.S. patent application Ser. No. 13/769,798, filed Feb. 18, 2013; U.S. patent application Ser. No. 13/769,779, filed Feb. 18, 2013; U.S. patent application Ser. No. 13/244,947 filed Sep. 26, 2011; PCT/US2012/57155, filed Sep. 25, 2012; U.S. application Ser. No. 13/244,946, filed Sep. 26, 2011; U.S. patent application Ser. No. 13/244,949, filed Sep. 26, 2011; and U.S. application Ser. No. 13/945,202, filed Jul. 18, 2013, the disclosures of which patents and patent applications are all hereby incorporated by reference in their entireties.

In embodiments of such methods, the nucleic acid target molecules amplified by the PCR amplification method comprise DNA. In embodiments of such methods, the nucleic acid target molecules amplified by the PCR amplification method comprise RNA. In embodiments, the nucleic acid may include uracil, and in embodiments may include dideoxyuracil (e.g., may include dideoxyuracil in place of a thymine during amplification). In embodiments of such methods, said second nucleic acid amplification method comprises an isothermal nucleic amplification method.

In embodiments of the methods disclosed herein, primers used in the amplification methods are directed to a single target nucleic acid sequence, and its complement. In embodiments of the methods disclosed herein, primers used in the amplification methods are directed to a plurality of target nucleic acid sequences, and complements thereof.

In embodiments, the target molecule is a RNA target, and cDNA molecules are generated from RNA target molecules by reverse transcription. These cDNA molecules provide substrate molecules for PCR amplification.

Optionally, the PCR amplification reaction first primer is at least 5, 6, 7, 8, 9, 10, 11, 12, 13, 14, 15, 20, 25, 30, 40, 50, or 60 and no more than 10, 11, 12, 13, 14, 15, 20, 25, 30, 40, 50, 60, 70, 80, 90, or 100 nucleotides in length, and wherein when the PCR amplification reaction first primer is annealed to the polynucleotide template, at least 1, 2, 3, 4, 5, 6, 7, 8, 9, or 10 nucleotides of the PCR amplification reaction first primer are mis-matched according to Watson-Crick base-pairing rules with corresponding nucleotides on the polynucleotide template. Optionally, the PCR amplification reaction second primer is at least 5, 6, 7, 8, 9, 10, 11, 12, 13, 14, 15, 20, 25, 30, 40, 50, or 60 and no more than 10, 11, 12, 13, 14, 15, 20, 25, 30, 40, 50, 60, 70, 80, 90, or 100 nucleotides in length, and wherein when the PCR amplification reaction second primer is annealed to the polynucleotide which is complementary to the polynucleotide template, at least 1, 2, 3, 4, 5, 6, 7, 8, 9, or 10 nucleotides of the PCR amplification reaction second primer are mis-matched according to Watson-Crick base-pairing rules with corresponding nucleotides on the polynucleotide which is complementary to the polynucleotide template.

In embodiments, PCR methods for amplifying a polynucleotide target molecule include: A) generating multiple copies of a polynucleotide template in a polymerase chain reaction (PCR) amplification reaction mixture, wherein the PCR amplification reaction mixture comprises a first PCR amplification reaction primer and a second PCR amplification reaction primer, wherein in the PCR amplification reaction mixture, the first PCR amplification reaction primer anneals to the polynucleotide template and the second PCR amplification reaction primer anneals to a polynucleotide which is complementary to the polynucleotide template, and wherein in the PCR amplification reaction mixture, multiple copies of a PCR amplification reaction product are formed, wherein the PCR amplification reaction product is a double-stranded nucleic acid molecule comprising a first strand and a second strand, and wherein a first strand of the PCR amplification reaction product is a copy of the polynucleotide template.

Applicant discloses herein methods for detecting Zika virus (ZIKV) in samples of bodily fluid. In embodiments, provided herein is a method for detecting ZIKV in a sample of bodily fluid, the method comprising: A) generating multiple complementary DNA (cDNA) copies of at least portions of ZIKV RNA, B) generating multiple copies of said cDNA copies of ZIKV RNA by polymerase chain reaction (PCR) amplification. In embodiments of the methods disclosed herein, generating multiple complementary DNA (cDNA) copies of at least portions of ZIKV RNA comprises using a reverse transcriptase to effect reverse transcription of said at least portions of ZIKV RNA to provide said cDNA copies of at least portions of ZIKV RNA. In embodiments of the methods for detecting Zika virus (ZIKV) in samples of bodily fluid disclosed herein, the PCR methods comprise reverse transcription PCR (RT-PCR) methods. In embodiments, said cDNA copies comprise a polynucleotide template for PCR amplification. In embodiments of the methods disclosed herein, generating multiple complementary DNA (cDNA) copies of at least portions of ZIKV RNA comprises PCR amplification using a PCR reaction mixture that comprises a PCR amplification reaction first primer and a PCR amplification reaction second primer, wherein in the PCR amplification reaction mixture, the PCR amplification reaction first primer anneals to the polynucleotide template and the PCR second primer anneals to a polynucleotide which is complementary to the polynucleotide template, and wherein in the PCR amplification reaction mixture, multiple copies of a PCR amplification reaction product are formed, wherein the PCR amplification reaction product is a double-stranded nucleic acid molecule comprising a first strand and a second strand, and wherein a first strand of the PCR amplification reaction product is a copy of the polynucleotide template. In embodiments of the methods for detecting Zika virus (ZIKV) in samples of bodily fluid disclosed herein, the PCR methods comprise real-time PCR methods. In embodiments of the methods for detecting Zika virus (ZIKV) in samples of bodily fluid disclosed herein, the PCR methods comprise reverse transcription real-time PCR methods.

The assays and methods disclosed herein may be performed on a device, or on a system, for processing a sample. The assays and methods disclosed herein can be readily incorporated into and used in device for processing a sample, or a system for processing a sample, which may be an automated assay device, or may be an automated assay system. Such a device, and such a system, may be useful for the practice of the methods disclosed herein. For example, a device may be useful for receiving a sample. A device may be useful for preparing, or for processing a sample. A device may be useful for performing an assay on a sample. A device may be useful for obtaining data from a sample. A device may be useful for transmitting data obtained from a sample. A device may be useful for disposing of a sample following processing or assaying of a sample.

A device may be part of a system, a component of which may be an automatic assay device. A device may be an automatic assay device. An automatic assay device may be configured to facilitate collection of a sample, prepare a sample for a clinical test, or effect a chemical reaction with one or more reagents or other chemical or physical processing, as disclosed herein. An automatic assay device may be configured to obtain data from a sample. An automatic assay device may be configured to transmit data obtained from a sample. An automatic assay device may be configured to analyze data from a sample. An automatic assay device may be configured to communicate with another device, or a laboratory, or an individual affiliated with a laboratory, to analyze data obtained from a sample.

A sample may be, for example, a blood sample (e.g., a sample obtained from a fingerstick, or from venipuncture, or an arterial blood sample), a urine sample, a biopsy sample, a tissue slice, stool sample, or other biological sample; a water sample, a soil sample, a food sample, an air sample; or other sample. A blood sample may comprise, e.g., whole blood, plasma, or serum. An automatic assay device may receive a sample from the subject through a housing of the device. The sample collection may occur at a sample collection site, or elsewhere. The sample may be provided to the device at a sample collection site.

Accordingly, Applicants disclose devices configured to measure ZIKV in a sample of blood according to a method disclosed herein. Devices configured to measure ZIKV in a sample of blood according to a method disclosed herein may be configured to determine ZIKV from a sample of blood that comprises no more than about 1000 µL of blood, or no more than about 500 µL of blood, no more than about 250 µL of blood, or no more than about 150 µL of blood, or no more than about 100 µL of blood, or no more than about 50 µL of blood, or, in embodiments, wherein said sample of blood comprises no more than about 25 µL of blood, or wherein said sample of blood comprises no more than about 10 µL, of blood, or wherein said sample of blood comprises less than about 10 µL of blood. Such devices may be configured to measure ZIKV in a sample of blood in less than about one hour, or, in embodiments, in less than about 40 minutes, or in less than about 30 minutes.

In some embodiments, an automatic assay device may be configured to accept or hold a cartridge. In some embodiments, an automatic assay device may comprise a cartridge. The cartridge may be removable from the automatic assay device. In some embodiments, a sample may be provided to the cartridge of the automatic assay device. Alternatively, a sample may be provided to another portion of an automatic assay device. The cartridge and/or device may comprise a sample collection unit that may be configured to accept a sample.

A cartridge may include a sample, and may include reagents for use in processing or testing a sample, disposables for use in processing or testing a sample, or other materials. Following placement of a cartridge on, or insertion of a cartridge into, an automatic assay device, one or more components of the cartridge may be brought into fluid communication with other components of the automatic assay device. For example, if a sample is collected at a cartridge, the sample may be transferred to other portions of the automatic assay device. Similarly, if one or more reagents are provided on a cartridge, the reagents may be transferred to other portions of the automatic assay device, or other components of the automatic assay device may be brought to the reagents. In some embodiments, the reagents or components of a cartridge may remain on-board the cartridge. In some embodiments, no fluidics are included that require tubing or that require maintenance (e.g., manual or automated maintenance).

A sample or reagent may be transferred to a device, such as an automatic assay device. A sample or reagent may be transferred within a device. Such transfer of sample or reagent may be accomplished without providing a continuous fluid pathway from cartridge to device. Such transfer of sample or reagent may be accomplished without providing a continuous fluid pathway within a device. In embodiments, such transfer of sample or reagent may be accomplished by a sample handling system (e.g., a pipette); for example, a sample, reagent, or aliquot thereof may be aspirated into an open-tipped transfer component, such as a pipette tip, which may be operably connected to a sample handling system which transfers the tip, with the sample, reagent, or aliquot thereof contained within the tip, to a location on or within the automatic assay device. The sample, reagent, or aliquot thereof can be deposited at a location on or within the automatic assay device. Sample and reagent, or multiple reagents, may be mixed using a sample handling system in a similar manner. One or more components of the cartridge may be transferred in an automated fashion to other portions of the automatic assay device, and vice versa.

A device, such as an automatic assay device, may have a fluid handling system. The fluid may be a sample, a reagent, diluent, wash, dye, or any other fluid that may be used by the device, and may include, but not limited to, homogenous fluids, different liquids, emulsions, suspensions, and other fluids. A fluid handling system, including without limitation a pipette, may also be used to transport vessels (with or without fluid contained therein) around the device. The fluid handling system may dispense or aspirate a fluid. The sample may include one or more particulate or solid matter floating within a fluid.

In embodiments, a fluid handling system may comprise a pipette, pipette tip, syringe, capillary, or other component. The fluid handling system may include one or more fluidically isolated or hydraulically independent units. For example, the fluid handling system may include one, two, or more pipette tips. The pipette tips may be configured to accept and confine a fluid. The tips may be fluidically isolated from or hydraulically independent of one another. The fluid contained within each tip may be fluidically isolated or hydraulically independent from one fluids in other tips and from other fluids within the device. The fluidically isolated or hydraulically independent units may be movable relative to other portions of the device and/or one another. The fluidically isolated or hydraulically independent units may be individually movable. A fluid handling system may comprise one or more base or support. A base or support may support one or more pipette or pipette units. A base or support may connect one or more pipettes of the fluid handling system to one another.

An automatic assay device may be configured to perform processing steps or actions on a sample obtained from a subject. Sample processing may include sample preparation, including, e.g., sample dilution, division of a sample into aliquots, extraction, contact with a reagent, filtration, separation, centrifugation, or other preparatory or processing action or step. An automatic assay device may be configured to perform one or more sample preparation action or step on the sample. Optionally, a sample may be prepared for a chemical reaction and/or physical processing step. A sample preparation action or step may include one or more of the following: centrifugation, separation, filtration, dilution, enriching, purification, precipitation, incubation, pipetting, transport, chromatography, cell lysis, cytometry, pulverization, grinding, activation, ultrasonication, micro column processing, processing with magnetic beads, processing with nanoparticles, or other sample preparation action or steps. For example, sample preparation may include one or more step to separate blood into serum and/or particulate fractions, or to separate any other sample into various components. Sample preparation may include one or more step to dilute and/or concentrate a sample, such as a blood sample, or other biological samples. Sample preparation may include adding an anti-coagulant or other ingredients to a sample. Sample preparation may also include purification of a sample. In embodiments, all sample processing, preparation, or assay actions or steps are performed by a single device. In embodiments, all sample processing, preparation, or assay actions or steps are performed within a housing of a single device. In embodiments, most sample processing, preparation, or assay actions or steps are performed by a single device, and may be performed within a housing of a single device. In embodiments, many sample processing, preparation, or assay actions or steps are performed by a single device, and may be performed within a housing of a single device. In embodiments, sample processing, preparation, or assay actions or steps may be performed by more than one device.

An automatic assay device may be configured to run one or more assay on a sample, and to obtain data from the sample. An assay may include one or more physical or chemical treatments, and may include running one or more chemical or physical reactions. An automatic assay device may be configured to perform one, two or more assays on a small sample of bodily fluid. One or more chemical reaction may take place on a sample having a volume, as described elsewhere herein. For example one or more chemical reaction may take place in a pill having less than femtoliter volumes. In an instance, the sample collection unit is configured to receive a volume of the bodily fluid sample equivalent to a single drop or less of blood or interstitial fluid. In embodiments, the volume of a sample may be a small volume, where a small volume may be a volume that is less than about 1000 µL, or less than about 500 µL, or less than about 250 µL, or less than about 150 µL, or less than about 100 µL, or less than about 75 µL, or less than about 50 µL, or less than about 40 µL, or less than about 20 µL, or less than about 10 µL, or other small volume. In embodiments, all sample assay actions or steps are performed on a single sample. In embodiments, all sample assay actions or steps are performed by a single device. In embodiments, all sample assay actions or steps are performed within a housing of a single device. In embodiments, most sample assay actions or steps are performed by a single device, and may be performed within a housing of a single device. In embodiments, many sample assay actions or steps are performed by a single device, and may be performed within a housing of a single device. In embodiments, sample processing, preparation, or assay actions or steps may be performed by more than one device.

An automatic assay device may be configured to perform a plurality of assays on a sample. In embodiments, an automatic assay device may be configured to perform a plurality of assays on a single sample. In embodiments, an automatic assay device may be configured to perform a plurality of assays on a single sample, where the sample is a small sample. For example, a small sample may have a sample volume that is a small volume of less than about 1000 µL, or less than about 500 µL, or less than about 250 µL, or less than about 150 µL, or less than about 100 µL, or less than about 75 µL, or less than about 50 µL, or less than about 40 µL, or less than about 20 µL, or less than about 10 µL, or other small volume. An automatic assay device may be capable of performing multiplexed assays on a single sample. A plurality of assays may be run simultaneously; may be run sequentially; or some assays may be run simultaneously while others are run sequentially. One or more control assays and/or calibrators (e.g., including a configuration with a control of a calibrator for the assay/tests) can also be incorporated into the device; control assays and assay on calibrators may be performed simultaneously with assays performed on a sample, or may be performed before or after assays performed on a sample, or any combination thereof. In embodiments, all sample assay actions or steps are performed by a single device. In embodiments, all of a plurality of assay actions or steps are performed within a housing of a single device. In embodiments, most sample assay actions or steps, of a plurality of assays, are performed by a single device, and may be performed within a housing of a single device. In embodiments, many sample assay actions or steps, of a plurality of assays, are performed by a single device, and may be performed within a housing of a single device. In embodiments, sample processing, preparation, or assay actions or steps may be performed by more than one device.

In embodiments, all of a plurality of assays may be performed in a short time period. In embodiments, such a short time period comprises less than about three hours, or less than about two hours, or less than about one hour, or less than about 40 minutes, or less than about 30 minutes, or less than about 25 minutes, or less than about 20 minutes, or less than about 15 minutes, or less than about 10 minutes, or less than about 5 minutes, or less than about 4 minutes, or less than about 3 minutes, or less than about 2 minutes, or less than about 1 minute, or other short time period.

An automatic assay device may perform nucleic acid assays, including isothermal nucleic acid assays (e.g., assays for detecting and measuring nucleic acid targets in a sample, including DNA and RNA targets). In embodiments, an automatic assay device may perform nucleic acid assays as disclosed in U.S. patent application Ser. No. 14/183,503, filed Feb. 18, 2014; U.S. patent application Ser. No. 14/214,850, filed Mar. 15, 2014; International Patent Application PCT/US2014/030034, filed Mar. 15, 2014; and in International Patent Application PCT/US2014/056151, filed Sep. 17, 2014. An automatic assay device may perform antibody assays, including enzyme-linked immunosorbent assays (ELISA), and other assays for detecting and measuring the amounts of proteins (including antibodies), peptides, and small molecules in samples. An automatic assay device may perform general chemistry assays, including electrolyte assays (e.g., assays for detecting and measuring the amounts of electrolytes such as sodium and potassium in a sample).

An automatic assay device may be configured to detect one or more signals relating to the sample. An automatic assay device may be configured to identify one or more properties of the sample. For instance, the automatic assay device may be configured to detect the presence or concentration of one analyte or a plurality of analytes or a disease condition in the sample (e.g., in or through a bodily fluid, secretion, tissue, or other sample). Alternatively, the automatic assay device may be configured to detect a signal or signals that may be analyzed to detect the presence or concentration of one or more analytes (which may be indicative of a disease condition) or a disease condition in the sample. The signals may be analyzed on board the device, or at another location. Running a clinical test may or may not include any analysis or comparison of data collected.

A chemical reaction or other processing step may be performed, with or without the sample. Examples of steps, tests, or assays that may be prepared or run by the device may include, but are not limited to immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidmetric assay, agglutination assay, radioisotope assay, viscometric assay, coagulation assay, clotting time assay, protein synthesis assay, histological assay, culture assay, osmolarity assay, and/or other types of assays, centrifugation, separation, filtration, dilution, enriching, purification, precipitation, pulverization, incubation, pipetting, transport, cell lysis, or other sample preparation action or steps, or combinations thereof. Steps, tests, or assays that may be prepared or run by the device may include imaging, including microscopy, cytometry, and other techniques preparing or utilizing images. Steps, tests, or assays that may be prepared or run by the device may further include an assessment of histology, morphology, kinematics, dynamics, and/or state of a sample, which may include such assessment for cells.

A device may be capable of performing all on-board steps (e.g., steps or actions performed by a single device) in a short amount of time. A device may be capable of performing all on-board steps on a single sample in a short amount of time. For example, from sample collection from a subject to transmitting data and/or to analysis may take about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, or 1 minute or less. The amount of time from accepting a sample within the device to transmitting data and/or to analysis from the device regarding such a sample may depend on the type or number of steps, tests, or assays performed on the sample. The amount of time from accepting a sample within the device to transmitting data and/or to analysis from the device regarding such a sample may take about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, or 1 minute or less.

A device may be configured to prepare a sample for disposal, or to dispose of a sample, such as a biological sample, following processing or assaying of a sample.

In embodiments, an automatic assay device may be configured to transmit data obtained from a sample. In embodiments, an automatic assay device may be configured to communicate over a network. An automatic assay device may include a communication module that may interface with the network. An automatic assay device may be connected to the network via a wired connection or wirelessly. The network may be a local area network (LAN) or a wide area network (WAN) such as the Internet. In some embodiments, the network may be a personal area network. The network may include the cloud. The automatic assay device may be connected to the network without requiring an intermediary device, or an intermediary device may be required to connect an automatic assay device to a network. An automatic assay device may communicate over a network with another device, which may be any type of networked device, including but not limited to a personal computer, server computer, or laptop computer; personal digital assistants (PDAs) such as a Windows CE device; phones such as cellular phones, smartphones (e.g., iPhone, Android, Blackberry, etc.), or location-aware portable phones (such as GPS); a roaming device, such as a network-connected roaming device; a wireless device such as a wireless email device or other device capable of communicating wireless with a computer network; or any other type of network device that may communicate possibly over a network and handle electronic transactions. Such communication may include providing data to a cloud computing infrastructure or any other type of data storage infrastructure which may be accessed by other devices.

An automatic assay device may provide data regarding a sample to, e.g., a health care professional, a health care professional location, such as a laboratory, or an affiliate thereof. One or more of a laboratory, health care professional, or subject may have a network device able to receive or access data provided by the automatic assay device. An automatic assay device may be configured to provide data regarding a sample to a database. An automatic assay device may be configured to provide data regarding a sample to an electronic medical records system, to a laboratory information system, to a laboratory automation system, or other system or software. An automatic assay device may provide data in the form of a report.

A laboratory, device, or other entity or software may perform analysis on data regarding a sample in real-time. A software system may perform chemical analysis and/or pathological analysis, or these could be distributed amongst combinations of lab, clinical, and specialty or expert personnel. Analysis may include qualitative and/or quantitative evaluation of a sample. Data analysis may include a subsequent qualitative and/or quantitative evaluation of a sample. Optionally, a report may be generated based on raw data, pre-processed data, or analyzed data. Such a report may be prepared so as to maintain confidentiality of the data obtained from the sample, the identity and other information regarding the subject from whom a sample was obtained, analysis of the data, and other confidential information. The report and/or the data may be transmitted to a health care professional. Data obtained by an automatic assay device, or analysis of such data, or reports, may be provided to a database, an electronic medical records system, to a laboratory information system (LIS), to a laboratory automation system (LAS), or other system or software.

Reagents

Applicant discloses reagents herein, where the reagents are suitable for identifying the presence of ZIKA virus in a sample, and are suitable for detecting ZIKA virus in a sample. Methods for identifying the presence of ZIKA virus in a sample, and for detecting ZIKA virus in a sample, include PCR nucleic acid amplification methods. In embodiments, the PCR nucleic acid amplification methods may be reverse transcription PCR methods. In embodiments, the PCR nucleic acid amplification methods may be real-time PCR methods. In embodiments, the PCR nucleic acid amplification methods may be real-time reverse transcription PCR methods.

A reagent for identifying the presence of ZIKA virus in a sample, the reagent comprising a nucleic acid primer comprising a nucleic acid sequence selected from the group SEQ ID NO: 1, SEQ ID NO: 2, SEQ ID NO: 3, SEQ ID NO: 4, SEQ ID NO: 5, and SEQ ID NO: 6, and a buffer. In embodiments, the nucleic acid primer comprises a nucleic acid sequence selected from the group SEQ ID NO: 1, SEQ ID NO: 2, SEQ ID NO: 3, and SEQ ID NO: 4.

A reagent for identifying the presence of ZIKA virus in a sample, the reagent comprising a variant of a nucleic acid primer comprising a nucleic acid sequence selected from the group SEQ ID NO: 1, SEQ ID NO: 2, SEQ ID NO: 3, SEQ ID NO: 4, SEQ ID NO: 5, and SEQ ID NO: 6, and a buffer, wherein the variant has at least about 95% sequence identity to the nucleic acid sequence. In embodiments, the a variant of a nucleic acid primer comprises a variant of a nucleic acid sequence selected from the group SEQ ID NO: 1, SEQ ID NO: 2, SEQ ID NO: 3, and SEQ ID NO: 4, wherein the variant has at least about 95% sequence identity to the nucleic acid sequence.

The reagent for identifying the presence of a ZIKA virus in a sample, wherein the buffer is selected from phosphate and TRIS. In embodiments, the buffer is TRIS.

The reagent comprising a primer and a buffer, wherein the primer comprises a reporter molecule.

The reagent comprising a primer and a buffer, wherein the primer comprises a reporter molecule, and wherein the reporter molecule comprises a fluorescent moiety, and the nucleic acid primer further comprises a quenching moiety effective to quench fluorescence from the fluorescent moiety when the primer is not hybridized to a target nucleic acid sequence.

Kits

A kit for identifying the presence of ZIKA virus in a sample, comprising a comprises a reagent including a nucleic acid primer, the primer comprising a nucleic acid sequence selected from the group SEQ ID NO: 1, SEQ ID NO: 2, SEQ ID NO: 3, SEQ ID NO: 4, SEQ ID NO: 5, and SEQ ID NO: 6, and a buffer.

In embodiments, a kit may comprise a reagent including a nucleic acid primer, the primer comprising a nucleic acid sequence selected from the group SEQ ID NO: 1, SEQ ID NO: 2, SEQ ID NO: 3, and SEQ ID NO: 4.

In embodiments, a kit for identifying the presence of ZIKA virus in a sample may include a reagent comprising a nucleic acid primer, the primer comprising a variant of a nucleic acid sequence selected from the group SEQ ID NO: 1, SEQ ID NO: 2, SEQ ID NO: 3, SEQ ID NO: 4, SEQ ID NO: 5, and SEQ ID NO: 6, and a buffer, wherein the variant has at least about 95% sequence identity to the nucleic acid sequence.

In embodiments, a kit for identifying the presence of ZIKA virus in a sample may include a reagent comprising a nucleic acid primer, the nucleic acid primer comprising a variant of a nucleic acid sequence selected from the group SEQ ID NO: 1, SEQ ID NO: 2, SEQ ID NO: 3, and SEQ ID NO: 4, and a buffer, wherein the variant has at least about 95% sequence identity to the nucleic acid sequence.

In embodiments, a kit for identifying the presence of ZIKA virus in a sample may include a reagent including a nucleic acid primer, wherein the nucleic acid primer comprises a reporter molecule.

In embodiments, a kit for identifying the presence of ZIKA virus in a sample may include a reagent including a primer with a reporter molecule, wherein the reporter molecule comprises a fluorescent moiety, and the nucleic acid primer further comprises a quenching moiety effective to quench fluorescence from the fluorescent moiety when the primer is not hybridized to a target nucleic acid sequence.

In embodiments, a kit for identifying the presence of ZIKA virus in a sample may include a reagent comprising a primer with a reporter molecule, wherein the reporter molecule comprises a fluorescent moiety, and the nucleic acid primer further comprises a quenching moiety effective to quench fluorescence from the fluorescent moiety when the primer is not hybridized to a target nucleic acid sequence.

In the following, abbreviations and acronyms have their standard meanings. For example, "mM" means millimolar; "uL" and "µL" mean microliter; "PFU/uL" means plaque forming units per uL; "mg/ml" means milligram per milliliter; "BSA" means bovine serum albumin; "cp/uL" means copies per microliter; and "1E4" means 1×10$^4$, the "E" indicating the exponent to the power of ten.

A kit for performing rRT-PCR for the detection of ZIKV contains primers and buffers. In embodiments, a kit includes the primers, probes, and positive and sample processing controls for use in PCR assays. In such an embodiment, the user needs to purchase commercially available enzymes, negative control and buffer.

In a first embodiments, a kit for detection of Zika contains primers and buffers and lacks enzymes, negative control, and buffer. Such a first embodiment of a kit for performing rRT-PCR for the detection of ZIKV may contain:

A) Sample processing control—MS2 bacteriophage supplied at 100× (200 PFU/uL), used at 1× concentration (2 PFU/uL). Formulation buffer for MS2: 10 mM Tris pH 7.5, 1 mM MgCl$_2$, 100 mM NaCl, 0.1% gelatin, 2 mg/ml BSA. Volume=80 uL.

B) Zika virus positive control—Synthetic RNA target designed via in vitro transcription of a g-block, supplied at 1E4 cp/uL, used at a final concentration of 4E3 cp/uL. Formulation buffer for positive control: 10 mM Tris pH 8.0, 0.1 mM EDTA (IDTE, IDT Cat No. 11-05-01-09), 1 unit/µL RNase inhibitor (RI, NEB Cat No. M0314S). Volume=250 uL per tube, 4 tubes provided.

C) Reagent A (Primer-probe mix)—comprises Zika primers (forward and reverse), MS2 primers (forward and reverse), Zika probe (FAM fluorophore, Dabcyl quencher), MS2 probe (SIMA-HEX fluorophore, Dabcyl quencher). Formulation buffer for primers and probes: 10 mM Tris pH 8.0, 0.1 mM EDTA (IDTE, IDT Cat No. 11-05-01-09) Volume=54 uL per tube, 4 tubes provided.

Reagent A includes Zika primers (forward and reverse) and Zika probe:

RLX 4877 GACATGGCTTCGGACAG (SEQ ID NO: 1)

RLX4878 ATATTGAGTGTCTGATTGCTTG (SEQ ID NO: 2)

RLX4879 FAM TGCCCAACACAAGGTGAAGCC Dabcyl (SEQ ID NO: 3)

Reagent A includes MS2 probe (SIMA-HEX fluorophore, Dabcyl quencher):

RLX 4943 AACGAGTCATATGAATTTAGGC (SEQ ID NO: 4)

RLX 4944 GCAGCCCGATCTATTTTATTAT (SEQ ID NO: 5)

RLX 5156 HEX AGGGAACGGAGTGTTTACAGTTCC Dabcyl (SEQ ID NO: 6)

This kit works with venous serum, venous plasma, venous whole blood and capillary whole blood matrices. This kit has been tested and found to be suitable for use in PCR assays. This kit is suitable for use on the following RT-PCR platforms: Roche LightCycler® 480 Instrument II; Bio Rad CFX96 Touch™ Real Time PCR Detection System; and ABI 7500 Fast Real Time RT PCR.

A suitable thermo-cycling program used for PCR for such a kit is illustrated in the following table:

| Temp | Time | Cycles |
| --- | --- | --- |
| 50° C. | 30 min | 1 |
| 95° C. | 15 min | 1 |
| 95° C. | 15 sec | 45 |
| 60° C. | 1 min * | |

Fluorescence is measured after each of the 45 cycles, as indicated by the asterisk (which indicates when fluorescence measurements are made).

In embodiments, an RT-PCR kit may include further components, including, for example, enzymes and additional controls (e.g., negative controls, sample processing controls, in addition to positive controls as provided in the kit embodiments discussed above).

In a second embodiment, an RT-PCR kit may comprise the following basic components: Enzymes—reverse transcriptase (RT) and DNA polymerase; Reaction buffer—containing $MgCl_2$ and dNTPs besides salt, buffer; Primers—DNA oligonucleotides; Probes—DNA oligonucleotides with 5'-fluorophore and 3'-quencher; and Controls—positive, negative, sample processing.

For example, such a second embodiment of a kit for performing rRT-PCR for the detection of ZIKV may contain:

Enzymes: reverse transcriptase; for example the following reverse transcriptase has the following amino acid sequence (SEQ ID NO: 7):
MTLNIEDEHRLHETSKEPDVSLGSTWLSDFPQAWAETGGMGLAVRQAPLI

IPLKATSTPVSIKQYPMSQEARLGIKPHIQRLLDQGILVPCQSPWNTPLL

PVKKPGTNDYRPVQDLREVNKRVEDIHPTVPNPYNLLSGPPPSHQWYTVL

DLKDAFFCLRLHPTSQPLFAFEWRDPEMGISGQLTWTRLPQGFKNSPTLF

NEALHRDLADFRIQHPDLILLQYVDDLLLAATSELDCQQGTRALLQTLGN

LGYRASAKKAQICQKQVKYLGYLLKEGQRWLTEARKETVMGQPTPKTPRQ

LREFLGTAGFCRLWIPGFAEMAAPLYPLTKTGTLFNWGPDQQKAYQEIKQ

ALLTAPALGLPDLTKPFELFVDEKQGYAKGVLTQKLGPRRRPVAYLSKKL

DPVAAGWPPCLRMVAAIAVLTKDAGKLTMGQPLVILAPHAVEALVKQPPD

RWLSNARMTHYQALLLDTDRVQFGPVVALNPATLLPLPEEGLQHNCLDIL

AEAHGTRPDLTDQPLPDADHTWYTDGSSLLQEGQRKAGAAVTTETEVIWA

KALPAGTSAQRAELIALTQALKMAEGKKLNVYTDSRYAFATAHIHGEIYR

RRGLLTSKGKEIKNKDEILALLKALFLPKRLSIIHCPGHQKGHSAEARGN

RMADQAARKAAITETPDTSTLL.

A suitable DNA Taq polymerase for use in a second embodiment of a kit as disclosed herein has the following amino acid sequence (SEQ ID NO: 8):
MGHHHHHHHHHHSSGHIEGRASSSGHENLYFQSMGMRGMLPLFEPKGRVL

LVDGHHLAYRTFHALKGLTTSRGEPVQAVYGFAKSLLKALKEDGDAVIVV

FDAKAPSFRHEAYGGYKAGRAPTPEDFPRQLALIKELVDLLGLARLEVPG

YEADDVLASLAKKAEKEGYEVRILTADKDLYQLLSDRIHVLHPEGYLITP

AWLWEKYGLRPDQWADYRALTGDESDNLPGVKGIGEKTARKLLEEWGSLE

ALLKNLDRLKPAIREKILAHMDDLKLSWDLAKVRTDLPLEVDFAKRREPD

RERLRAFLERLEFGSLLHEFGLLESPKALEEAPWPPPEGAFVGFVLSRKE

PMWADLLALAAARGGRVHRAPEPYKALRDLKEARGLLAKDLSVLALREGL

GLPPGDDPMLLAYLLDPSNTTPEGVARRYGGEWTEEAGERAALSERLFAN

LWGRLEGEERLLWLYREVERPLSAVLAHMEATGVRLDVAYLRALSLEVAE

EIARLEAEVERLAGHPFNLNSRDQLERVLEDELGLPAIGKTEKTGKRSTS

AAVLEALREAHPIVEKILQYRELTKLKSTYIDPLPDLIHPRTGRLHTRFN

QTATATGRLSSSDPNLQNIPVRTPLGQRIRRAFIAEEGWLLVALDYSQIE

LRVLAHLSGDENLIRVFQEGRDIHTETASWMEGVPREAVDPLMIRRAAKT

INFGVLYGMSAHRLSQELAIPYEEAQAFIERYFQSFPKVRAWIEKTLEEG

RRRGYVETLFGRRRYVPDLEARVKSVREAAERMAFNMPVQGTAADLMKLA

MVKLEPRLEEMGARMLLQVHDELVLEAPKERAEAVARLAKEVMEGVYPLA

VPLEVEVGIGEDWLSAKE.

A suitable formulation buffer for use in a second embodiment of a kit as disclosed herein may be: 20 mM Tris pH 7.5, 300 mM KCl, 2 mM DTT, 0.1 mM EDTA, 50% Glycerol, 0.2% Triton X-100.

Thermal cycling parameters for PCR assays using reagents of a second embodiment of a kit disclosed herein are presented in the following table. It will be understood that the number of cycles can be adjusted as desired; for example, the number of cycles may be decreased from 60 to 45-50.

| PCR cycle | | |
| --- | --- | --- |
| Temp | Time | Cycles |
| 56° C. | 10 mm | 1x |
| 95° C. | 1 min | 1x |
| 95° C. | 15 sec | 60x |
| 64° C. | 1 min* | |

The asterisk indicates that fluorescence may be measured after this step.

A reagent for use in a second embodiment of a kit having features as disclosed herein may be termed a "mastermix" and may have a composition as described in the following table:

| | Units | [Stock] | [Final] | # of reactions 1 | # of reactions 60 |
| --- | --- | --- | --- | --- | --- |
| water | | | | 7.01 | 420.6 |
| NEB 5X HF Phusion Buffer | X | 5 | 1 | 5 | 300 |
| dNTP | mM | 10 | 0.2 | 0.5 | 30 |
| BSA | X | 100 | 3.5 | 0.88 | 52.5 |
| MS2 Forward primer | uM | 150 | 1 | 0.17 | 10 |
| MS2 Reverse primer | uM | 150 | 1 | 0.17 | 10 |
| MS2 probe | uM | 25 | 0.3 | 0.3 | 18 |
| Zika Forward primer | uM | 150 | 1 | 0.17 | 10 |
| Zika Reverse primer | uM | 150 | 1 | 0.17 | 10 |
| Zika probe | uM | 25 | 0.3 | 0.3 | 18 |
| RT RDP205 | mg/mL | 0.1 | 0.0005 | 0.13 | 7.5 |
| His-tagged Taq (RDP282B) | mg/mL | 0.25 | 0.002 | 0.2 | 12 |
| template | | | | 10 | 600 |
| total | | | | 25 | 1500 |
| Total MM (no template) | | | | 15 | 900 |

The buffer indicated in the table above is Phusion® HF Buffer (NEB, catalog# B0518S) used after five-fold dilution.

A second embodiment of a kit having features as disclosed herein may include dNTPs, which may be provided in solution, or may be provided in dry (powdered) form.

A second embodiment of a kit having features as disclosed herein may include BSA, for example, BSA for use following 100-fold dilution. BSA may be provided in, and/or may be diluted in, a formulation buffer, such as the following formulation buffer: 20 mM $KPO_4$ pH 7.0, 50 mM NaCl, 0.1 mM EDTA, 5% Glycerol.

Kits as disclosed herein may be stored at −20° C. In embodiments, kits as disclosed herein may be stored at other temperatures, such as, e.g., at 0-4° C.; and at room temperature.

EXAMPLE

Thermal cycling protocols for polymerase chain reactions for nucleic acid amplification may include, for example: about 5 to 20 minutes at "low temperature" such as a temperature of between about 45° C. and about 55° C., followed by about 1-15 minute at "high temperature" such as a temperature of between about 80° C. to about 95° C., followed by about 20 to 100 thermal cycles, where each thermal cycle consists of about 10 to 120 seconds at "high temperature" then about 1 to 15 minutes at "low temperature". In some PCR methods, an "intermediate temperature" of between about 60° C. and about 74° C. may be applied, e.g., between applications of "low temperature" and applications of "high temperature".

FIG. 1 shows components of a kit having features disclosed herein (e.g., a Zika RT-PCR kit). The box with labeling on the outside is shown in a closed configuration (on the right). The box with reagent vials is shown in an open configuration (central box in the figure) with the lid open and showing reagent vials in place in receptacles within the box. The contents of the reagent vials provide an integrated set of reagents to perform the assay. The kit may also include capillary sample collection devices and a shipment container. Shown in FIG. 1B are an open shipment container for transporting the samples stably, with each sample held in a Nanotainer™ (the left-most box in the figure), and three sample collection devices (shown in the center foreground of the figure).

Figure 2:
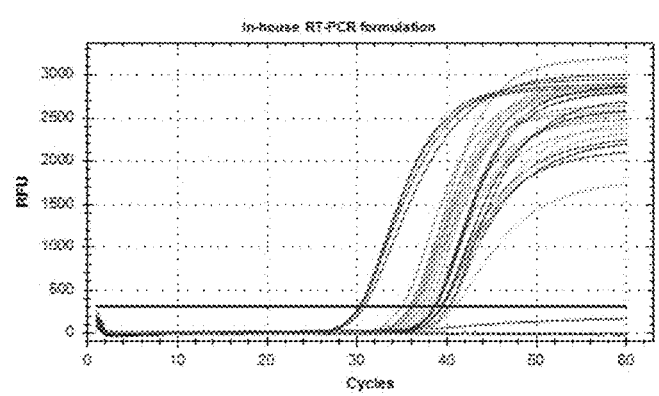
FIG. 2 is a plot of fluorescence (a measure of the numbers of cDNA copies of the target nucleic acid sequence) versus time (as cycles) showing the results of rRT-PCR amplification of Zika virus.

FIG. 2 provides results of a RT-PCR assays performed using reagents and using automated sample analysis devices and systems as disclosed herein.

The primers used in the nucleic acid amplification Zika assay were designed from a consensus of a multi-sequence alignment of all Zika strains deposited in GenBank. The gene target we selected is a 100-base pair region within the highly conserved polyprotein gene.

Figure 3:
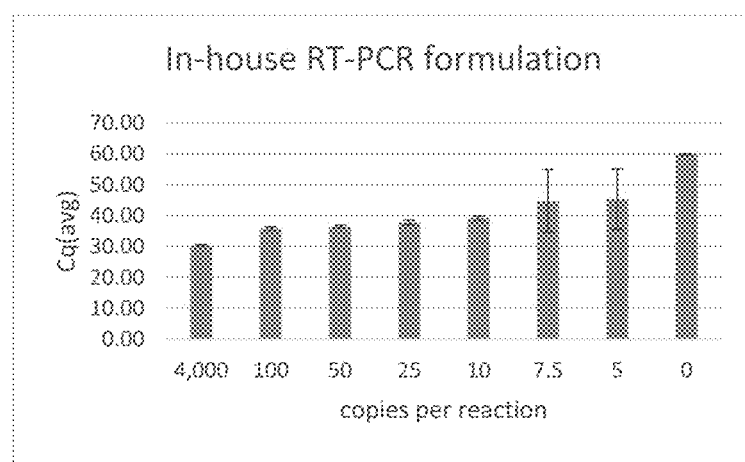
FIG. 3 is a graph showing the copies resulting from rRT-PCR amplification of Zika virus.

FIG. 3 presents inflection time measurements (average of four replicates) showing the average inflection time on the vertical axis plotted against the number of copies of the nucleic acid target sequences in the sample that was analyzed.

An example of a suitable thermal cycling protocol useful for the polymerase chain reaction portion of the rRT-PCR amplification is: 10 minutes at 50° C., followed by 1 minute at 95° C., followed by 60 thermal cycles; each thermal cycle consisted of 15 seconds at 95° C. then 1 minute at 64° C.

For further example, the following thermal cycling protocol was used for the polymerase chain reaction portion of the rRT-PCR amplification: 30 minutes at 50° C., followed by 15 minutes at 95° C., followed by 45 thermal cycles; each thermal cycle consisted of 15 seconds at 95° C. then 1 minute at 60° C. Following the last thermal cycle (after the final 1 minute at 60° C.), fluorescence measurements may be taken.

Reagents suitable for use in PCR amplification methods include:

TABLE 2

RT-PCR formulation

| RT-PCR Master Mix | Units | [Stock] | [Final] | # of reactions 1 | # of reactions 60 |
|---|---|---|---|---|---|
| water | | | | 7.62 | 457.00 |
| NEB 5X HF Phusion Buffer | X | 5 | 1 | 5.00 | 300.00 |
| dNTP | mM | 10 | 0.2 | 0.50 | 30.00 |
| BSA | X | 100 | 3.5 | 0.88 | 52.50 |
| Zika F RLX4877 | uM | 150 | 1 | 0.17 | 10.00 |
| Zika R RLX4878 | uM | 150 | 1 | 0.17 | 10.00 |
| Zika probe RLX4879 | uM | 25 | 03 | 0.30 | 18.00 |
| RT RDP205 | mg/mL | 0.1 | 0.0005 | 0.13 | 7.50 |
| His-tagged Taq (RDP282) | mg/mL | 0.25 | 0.0025 | 0.25 | 15.00 |
| template | | | | 10 | 600 |
| total | | | | 25 | 1500 |
| Total MM (no template) | | | | 15.00 | 900.00 |

5× Phusion buffer (HF & CG, ("high fidelity" and CG-rich) from New England BioLabs (NEB) contains 7.5 mM MgCl$_2$ (1.5 mM at 1×(i.e., no) dilution).

Primer sequences used to identify ZIKV in a sample were:

TABLE 3

| RLX 4877 | GACATGGCTTCGGACAG | SEQ ID NO: 1 |
| RLX4878 | ATATTGAGTGTCTGATTGCTTG | SEQ ID NO: 2 |
| RLX4879 | FAM TGCCCAACACAAGGTGAAGCC Dabcyl | SEQ ID NO: 3 |

Primer sequences used to identify MS2 in a sample were:

TABLE 4

| RLX 4943 | AACGAGTCATATGAATTTAGGC | SEQ ID NO: 4 |
| RLX 4944 | GCAGCCCGATCTATTTTATTAT | SEQ ID NO: 5 |
| RLX 5156 | HEX AGGGAACGGAGTGTTTACAGTTCC Dabcyl | SEQ ID NO: 6 |

As shown, FIG. 2 shows the results of a RT-PCR amplification of Zika virus, as relative fluorescence units (RFU) plotted against cycles (thermal cycles).

FIG. 2 is a plot of fluorescence (a measure of the numbers of cDNA copies of the target nucleic acid sequence) versus time (as cycles) showing the results of rRT-PCR amplification of Zika virus.

The average Cq was calculated from four Cq measurements for different numbers of copies per reaction. These results are presented in the following table (Table 5):

TABLE 5

| T276A1 c/rxn in neg. sample prep | In-house RT-PCR formulation | | | | | |
|---|---|---|---|---|---|---|
| | Cq1 | Cq2 | Cq3 | Cq4 | Cq(avg) | Stdev |
| 4,000 | 30.72 | 30.25 | 30.19 | 30.39 | 30.39 | 0.24 |
| 100 | 36.31 | 35.95 | 34.97 | 35.74 | 35.74 | 0.57 |
| 50 | 36.29 | 36.32 | 37.14 | 36.10 | 36.46 | 0.46 |
| 25 | 38.15 | 36.77 | 38.65 | 37.68 | 37.81 | 0.80 |
| 10 | 39.37 | 40.13 | 38.69 | 38.50 | 39.17 | 0.74 |
| 7.5 | 39.44 | 60.00 | 39.29 | 40.16 | 44.72 | 10.19 |
| 5 | 40.80 | 40.35 | 40.25 | 60.00 | 45.35 | 9.77 |
| 0 | 60.00 | 60.00 | 60.00 | 60.00 | 60.00 | 0.00 |

FIG. 3 is a graph showing the average numbers of copies resulting from rRT-PCR amplification of Zika virus as a function of copies per reaction.

As shown, FIG. 3 shows average Cq versus copies per reaction.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications and patent applications mentioned herein are incorporated herein by reference to disclose and describe the structures and/or methods in connection with which the publications and/or patent applications are cited.

The invention claimed is:

1. A kit for identifying the presence of ZIKA virus in a sample, comprising a nucleic acid primer comprising a nucleic acid sequence selected from the group SEQ ID NO: 1, SEQ ID NO: 2, SEQ ID NO: 3, SEQ ID NO: 4, SEQ ID NO: 5, and SEQ ID NO: 6, and a buffer.

2. The kit of claim 1, wherein the nucleic acid primer comprises a nucleic acid sequence selected from the group SEQ ID NO: 1, SEQ ID NO: 2, and SEQ ID NO: 3.

3. A kit for identifying the presence of ZIKA virus in a sample, comprising a nucleic acid primer comprising a variant of a nucleic acid sequence selected from the group SEQ ID NO: 1, SEQ ID NO: 2, SEQ ID NO: 3, SEQ ID NO: 4, SEQ ID NO: 5, and SEQ ID NO: 6, and a buffer, wherein the variant has at least about 95% sequence identity to the nucleic acid sequence.

4. The kit of claim 3, wherein the nucleic acid primer comprises a nucleic acid primer comprising a variant of a nucleic acid sequence selected from the group SEQ ID NO: 1, SEQ ID NO: 2, and SEQ ID NO: 3, and a buffer, wherein the variant has at least about 95% sequence identity to the nucleic acid sequence.

5. The kit of claim 1, wherein the buffer is selected from phosphate, tris(hydroxymethyl)aminomethane (TRIS), 3-(N-morpholino) propanesulfonic acid (MOPS), 3-morpholino-2-hydroxypropanesulfonic acid (MOPSO), 2-(N-morpholino)ethanesulfonic acid (IVIES), N-(2-Acetamido)-iminodiacetic acid (ADA), and piperazine-N,N'-bis(2-ethanesulfonic acid) (PIPES).

6. The kit of claim 2, wherein the buffer is tris(hydroxymethyl)aminomethane (TRIS).

7. The kit of claim 1, further comprising a reporter molecule.

8. The kit of claim 2, further comprising a reporter molecule.

9. The kit of claim 3, further comprising a reporter molecule.

10. The kit of claim 4, further comprising a reporter molecule.

11. The kit of claim 1, wherein the nucleic acid primer comprises a reporter molecule.

12. The kit of claim 2, wherein the nucleic acid primer comprises a reporter molecule.

13. The kit of claim 3, wherein the nucleic acid primer comprises a reporter molecule.

14. The kit of claim 4, wherein the nucleic acid primer comprises a reporter molecule.

15. The kit of claim 11, wherein the reporter molecule comprises a fluorescent moiety, and the nucleic acid primer further comprises a quenching moiety effective to quench fluorescence from the fluorescent moiety when the primer is not hybridized to a target nucleic acid sequence.

16. The kit of claim 12, wherein the reporter molecule comprises a fluorescent moiety, and the nucleic acid primer further comprises a quenching moiety effective to quench fluorescence from the fluorescent moiety when the primer is not hybridized to a target nucleic acid sequence.

17. The kit of claim 13, wherein the reporter molecule comprises a fluorescent moiety, and the nucleic acid primer further comprises a quenching moiety effective to quench fluorescence from the fluorescent moiety when the primer is not hybridized to a target nucleic acid sequence.

18. The kit of claim 14, wherein the reporter molecule comprises a fluorescent moiety, and the nucleic acid primer further comprises a quenching moiety effective to quench fluorescence from the fluorescent moiety when the primer is not hybridized to a target nucleic acid sequence.

19. A kit for identifying the presence of ZIKA virus in a sample, comprising a nucleic acid primer comprising a variant of a nucleic acid sequence selected from the group SEQ ID NO: 1, SEQ ID NO: 2, SEQ ID NO: 3, SEQ ID NO: 4, SEQ ID NO: 5, and SEQ ID NO: 6, and a buffer, wherein the variant has at least about 90% sequence identity to the nucleic acid sequence.

20. The kit of claim 19, further comprising a reporter molecule, wherein the reporter molecule comprises a fluorescent moiety, and the nucleic acid primer further comprises a quenching moiety effective to quench fluorescence from the fluorescent moiety when the primer is not hybridized to a target nucleic acid sequence.

* * * * *